United States Patent
Weiss

(10) Patent No.: US 11,084,867 B2
(45) Date of Patent: Aug. 10, 2021

(54) REGENERATION OF DAMAGED TISSUE

(71) Applicant: Elastagen Pty Ltd, Eveleigh (AU)

(72) Inventor: Anthony Steven Weiss, Sydney (AU)

(73) Assignee: ALLERGAN PHARMACEUTICALS INTERNATIONAL LIMITED, Dublin (IE)

( * ) Notice: Subject to any disclaimer, the term of this patent is extended or adjusted under 35 U.S.C. 154(b) by 0 days.

(21) Appl. No.: 16/169,908

(22) Filed: Oct. 24, 2018

(65) Prior Publication Data

US 2019/0062405 A1    Feb. 28, 2019

Related U.S. Application Data

(63) Continuation of application No. 14/911,401, filed as application No. PCT/AU2014/050180 on Aug. 13, 2014, now abandoned.

(30) Foreign Application Priority Data

Aug. 13, 2013  (AU) ................................ 2013903092

(51) Int. Cl.
*A61F 13/00*  (2006.01)
*A61F 13/02*  (2006.01)
(Continued)

(52) U.S. Cl.
CPC ........ *C07K 14/78* (2013.01); *A61F 13/00063* (2013.01); *A61F 13/0213* (2013.01); *A61K 9/0014* (2013.01); *A61K 9/06* (2013.01); *A61K 9/70* (2013.01); *A61K 38/39* (2013.01); *A61L 27/22* (2013.01); *A61L 27/3633* (2013.01);
(Continued)

(58) Field of Classification Search
CPC .......... A61F 13/00063; A61F 13/0213; A61K 9/0014; A61K 9/06; A61K 9/70; A61K 38/00; A61K 38/39; A61L 27/22; A61L 27/3633; A61L 27/56; A61L 2400/06; A61P 17/02; A61P 41/00; C07K 14/78
See application file for complete search history.

(56) References Cited

U.S. PATENT DOCUMENTS

4,947,840 A    8/1990  Yannas et al.
5,260,203 A    11/1993  Lardner et al.
(Continued)

FOREIGN PATENT DOCUMENTS

EP    0210846    2/1987
EP    0480048    4/1992
(Continued)

OTHER PUBLICATIONS

Rnjak et al., Severe Burn Injuries and the Role of Elastin in the Design of Dermal Substitutes, 2011, Tissue Engineering: Part B, vol. 17, No. 2, pp. 81-92 (Year: 2011).*

(Continued)

*Primary Examiner* — Trevor Love
(74) *Attorney, Agent, or Firm* — Nathan S. Smith; Christopher J. Betti; Morgan, Lewis & Bockius LLP

(57) ABSTRACT

A method of healing a wound including contacting a wound edge with a tropoelastin or elastin derived peptide in conditions for enabling a sustained contact of the tropoelastin with the wound edge for a time period for enabling re-epithelialization of the wound.

11 Claims, 4 Drawing Sheets

(51) Int. Cl.

| | | |
|---|---|---|
| *A61K 9/00* | (2006.01) | |
| *A61K 9/06* | (2006.01) | |
| *A61K 9/70* | (2006.01) | |
| *A61K 38/00* | (2006.01) | |
| *A61K 38/39* | (2006.01) | |
| *A61L 27/22* | (2006.01) | |
| *A61L 27/26* | (2006.01) | |
| *A61L 27/56* | (2006.01) | |
| *A61P 17/02* | (2006.01) | |
| *A61P 41/00* | (2006.01) | |
| *C07K 14/78* | (2006.01) | |
| *A61L 27/36* | (2006.01) | |

(52) U.S. Cl.
CPC .............. *A61L 27/56* (2013.01); *A61K 38/00* (2013.01); *A61L 2400/06* (2013.01)

(56) References Cited

U.S. PATENT DOCUMENTS

| | | |
|---|---|---|
| 5,726,040 A | 3/1998 | Ensley et al. |
| 5,969,106 A | 10/1999 | Rothstein |
| 6,232,458 B1 | 5/2001 | Weiss et al. |
| 6,248,516 B1 | 6/2001 | Winter et al. |
| 7,001,328 B1 | 2/2006 | Barofsky |
| 7,125,960 B2 | 10/2006 | Keiichi |
| 7,192,043 B1 | 3/2007 | Weiss |
| 7,618,935 B2 | 11/2009 | Hill et al. |
| 7,770,126 B2 | 4/2010 | Ng et al. |
| 7,803,577 B2 | 9/2010 | Weiss |
| 8,038,991 B1 | 10/2011 | Stankus |
| 8,101,717 B2 | 1/2012 | Weiss et al. |
| 8,383,158 B2 | 2/2013 | Michal et al. |
| 8,518,105 B2 | 8/2013 | Hossainy et al. |
| 8,974,803 B2 | 2/2015 | Weiss |
| 2003/0166848 A1 | 9/2003 | Rothstein |
| 2004/0110439 A1 | 6/2004 | Chaikof et al. |
| 2004/0253220 A1 | 12/2004 | Perrier et al. |
| 2004/0258676 A1 | 12/2004 | Perrier et al. |
| 2004/0267362 A1 | 12/2004 | Hwang et al. |
| 2005/0244393 A1 | 11/2005 | Philipart et al. |
| 2006/0115457 A1 | 6/2006 | Hnojewyj |
| 2007/0005148 A1 | 1/2007 | Barofsky |
| 2007/0237735 A1 | 10/2007 | Denommee et al. |
| 2007/0287741 A1 | 12/2007 | Herzberg |
| 2009/0035251 A1 | 2/2009 | Wortzman et al. |
| 2009/0169593 A1 | 7/2009 | Gergory et al. |
| 2009/0226519 A1 | 9/2009 | Claude et al. |
| 2010/0004699 A1 | 1/2010 | Alleyne et al. |
| 2010/0021440 A1 | 1/2010 | Weiss et al. |
| 2010/0040710 A1 | 2/2010 | Perrier et al. |
| 2010/0159008 A1 | 6/2010 | Barron et al. |
| 2010/0247454 A1 | 9/2010 | Mitts et al. |
| 2011/0223230 A1 | 9/2011 | Hersel et al. |
| 2011/0229574 A1 | 9/2011 | Guillen |
| 2012/0220691 A1 | 8/2012 | Shreiber et al. |
| 2013/0071500 A1 | 3/2013 | Kizoulis et al. |
| 2013/0164340 A1 | 6/2013 | Ensley et al. |
| 2013/0296528 A1 | 11/2013 | Sommer-Knudsen |
| 2014/0235547 A1 | 8/2014 | Mithieux et al. |

FOREIGN PATENT DOCUMENTS

| | | |
|---|---|---|
| JP | 2012-519713 | 8/2012 |
| JP | 2016-527979 | 9/2016 |
| WO | WO 94/007921 | 4/1994 |
| WO | WO 94/014958 | 7/1994 |
| WO | WO 98/06830 | 2/1998 |
| WO | WO 98/034563 | 8/1998 |
| WO | WO 98/044001 | 10/1998 |
| WO | WO 99/003886 | 1/1999 |
| WO | WO 99/011196 | 3/1999 |
| WO | WO 00/004043 | 1/2000 |
| WO | WO 00/073399 | 12/2000 |
| WO | WO 01/036000 | 5/2001 |
| WO | WO 01/056595 | 8/2001 |
| WO | WO 2004/091592 | 10/2004 |
| WO | WO 2006/101441 | 9/2006 |
| WO | WO 2007/029913 | 3/2007 |
| WO | WO 2008/020329 | 2/2008 |
| WO | WO 2008/033847 | 3/2008 |
| WO | WO 2008/037028 | 4/2008 |
| WO | WO 2008/058323 | 5/2008 |
| WO | WO 2009/015372 | 1/2009 |
| WO | WO 2009/034559 | 3/2009 |
| WO | WO 2006/098024 | 8/2009 |
| WO | WO 2009/099570 | 8/2009 |
| WO | WO 2010/102337 | 9/2010 |
| WO | WO 2011/127478 | 10/2011 |
| WO | WO 2012/068619 | 5/2012 |
| WO | WO 2012/080706 | 6/2012 |
| WO | WO 2013/044314 | 4/2013 |
| WO | WO 2014/063194 | 5/2014 |
| WO | WO 2014/089610 | 6/2014 |
| WO | WO 2015/042639 | 4/2015 |

OTHER PUBLICATIONS

Akhtar et al., "Oxidative and Nitrosative Modifications of Tropoelastin Prevent Elastic Fiber Assembly in Vitro," 2010, J. Biol. Chem., 285:37396-37404.

Albertine et al., "Chronic lung disease in preterm lambs: effect of daily vitamin A treatment on alveolarization," 2010 Am J Physiol Lung Cell Mol., 299(1):59-72.

Almine et al., "Elastin Signaling in Wound Repair," 2012, Birth Defects Research, 96:248-257.

Al-Obeidi et al., "Peptide and Peptidomimetic Libraries," 1998, Mol Biotechnol, pp. 205-223.

Altschul et al., "Basic Local Alignment Search Tool," 1990, J Mol Biol, 215:403-410.

Altschul et al., "Gapped BLAST and PSI-BLAST: a new generation of protein database search programs," 1997, Nucleic Acids Res, 25(17):3389-3402.

Amann et al., "ATG vectors for regulated high-level expression of cloned genes in *Escherichia coli*," 1985, Gene, 40:183-190.

Anderson et al., "Biomaterial microarrays: rapid, microscale screening of polymer-cell interaction," 2005, Biomaterials 26:4892-4897.

Anderson et al., "Nanoliter-scale synthesis of arrayed biomaterials and application to human embryonic stem cells," 2004, Nature Biotechnology, 22(7):863-866.

Annabi et al., "Cross-linked open-pore elastic hydrogels based on tropoelastin, elastin and high pressure CO2," 2010, Biomaterials, 31:1655-1665.

Annabi et al., "Synthesis of highly porous crosslinked elastin hydrogels and their interaction with fibroblasts in vitro," 2009, Biomaterials, 30:4550-4557.

Annabi et al., "The fabrication of elastin-based hydrogels using high pressure CO2," 2009 , Biomaterials, 30:1-7.

Aubin et al., "Directed 3D cell alignment and elongation in microengineered hydrogels," 2010, Biomaterials, 31:6941-6951.

Ayers et al., "Elastin-Based Side Chain Polymers Synthesized by ATRP," 2003, Macromolecules, 36:5967-5973.

Ayers et al., "Stimulus Responsive Behavior of Elastin-Abased Side Chain Polymers," 2005, Macromolecules, 38:1699-1704.

Baar et al., "Self-organization of rat cardiac cells into contractile 3-D cardiac tissue," 2005, The FASEB Journal, 19:275-277.

Bae et al., "Cell-laden microengineered pullulan methacrylate hydrogels promote cell proliferation and 3D cluster formation," 2011, Soft Matter, 7:1903-1911.

Bax et al., "Cell Adhesion to Tropoelastin is Mediated via the C-terminal GRKRK Motif and Integrin," Journal of Biological Chemistry, 2009, 284(42):28616-28623.

Bedell-Hogan et al., "Oxidation Crosslinking and Insolubilization of Recombinant Tropoelastin by Purified Lysyl Oxidase," 1993, J of Biol Chem, 268(14):10345-10350.

Bellingham et al., "Recombinant Human Elastin Polypeptides Self-Assemble into Biomaterials with Elastin-Like Properties," 2003, Biopolymers, 70:445-455.

(56) References Cited

OTHER PUBLICATIONS

Bjellqvist et al., "A nonlinear wide-range immobilized pH gradient for two-dimensional electrophoresis and its definition in a relevant pH scale," 1993, Electrophoresis, 14:1357-1365.
Boateng et al., "RGD and YIGSR synthetic peptides facilitate cellular adhesion identical to that of laminin and fibronectin but alter the physiology of neonatal cardiac myocytes," 2005, American Journal of Physiology—Cell Physiology, 288:C30-C38.
Brammer et al., "Improved bone-forming functionality on diameter-controlled TiO2 nanotube surface," 2009, Acta Biomaterialia, 5:3215-3223.
Broekelmann et al., "Tropoelastin Interacts with Cellsurface Glycosaminoglycans via Its COOHterminal Domain," 2005, J of Biol Chem, 280(49):40939-40947.
Cenizo et al., "LOXL as a target to increase the elastin content in adult skin: a dill extract induces the LOXL gene expression," 2006, Exp Dermatol, 15(8):574-581.
Charest et al., "Myoblast alignment and differentiation on cell culture substrates with microscale topography and model chemistries," 2007, Biomaterials, 28:2202-2210.
Chen et al., "Fibulin-4 regulates expression of the tropoelastin gene and consequent elastic-fibre formation by human fibroblasts," 2009, J Biochem, 423:79-89.
Chung et al., "A rapid and convenient method for the preparation and storage of competent bacterial cells," 1988, Nucleic Acids Res., 16(8):3580.
Cleary et al., "Elastic Tissue, Elastin and Elastin Associated Microfibrils," 1996, Extracellular Matrix, vol. 2, p. 95.
Eastoe, "The Amino Acid Composition of Mammalian Collagen and Gelatin," 1955, Biochemical Journal, 61:589-600.
Falcone et al., "Crosslinked hyaluronic acid dermal fillers: a comparison of rheological properties," 2008, Journal of Biomedical Materials Research, 87A, pp. 264-271.
Falsey et al., "Peptide and Small Molecule Microarray for High Throughput Cell Adhesion and Functional Assays," 2001, Bioconjugate Chemistry, 12:346-353.
Fazio et al., "Isolation and Characterization of Human Elastin cDNAs and Age Associated Variation in Elastin Gene Expression in Cultured Skin Fibroblasts," 1988, Laboratory Investigation, 58(3):270-277.
Feinberg et al., "Muscular Thin Films for Building Actuators and Powering Devices," 2007, Science, 317:1366-1370.
Fornieri et al., "Lysyl Oxidase Activity and Elastin/Glycosaminoglycan Interactions in Growing Chick and Rat Aortas," 1987, J of Cell Biology, 105:1463-1469.
GenBank: A52896.1 (1997) Sequence 12 from Patent WO9625506, 1 page.
GenBank: ACC13884.1 (2000) elastin partial [*Homo sapiens*], 1 page.
GenBank: ACC98394.1 (2002) elastin [*Homo sapiens*], 1 page.
Giraud et al., "Current State of the Art in Myocardial Tissue Engineering," 2007, Tissue Engineering, 13(8):1825-1836.
Haedersdal et al., "Fractional CO2 Laser Assisted Drug Delivery," 2010, Lasers in Surgery and Medicine, 42:113-122.
Hashimoto et al., "Development of alginate wound dressings linked with hybrid peptides derived from laminin and elastin," 2004, Biomaterials, 25:1407-1414.
Hill et al., "cpnDB: a Chaperonin Sequence Database," 2004, Genome Res. 14:1669-1675.
Hruby et al., "Synthesis of oligopeptide and peptidomimetic libraries," 1997, Curr Opin Chem Biol 1:114-119.
Huang et al., "Inhibition of Versican Synthesis by Antisense Alters Smooth Muscle Cell Phenotype and Induces Elastic Fiber Formation in Vitro and in Neointima After Vessel Injury," 2006, Circ Res, 98(3):370-377.
Hwang et al., "Retrovirally Mediated Overexpression of Glycosaminoglycan-Deficient Biglycan in Arterial Smooth Muscle Cells Induces Tropoelastin Synthesis and Elastic Fiber Formation in Vitro and in Neointimae after Vascular Injury," 2008, Am J Pathol, 173(6):1919-1928.
Indik et al, "Production of Recombinant Human Tropoelastin: Characterization and Demonstration of Immunologic and Chemotactic Activity," 1990, Archives of Biochemistry and Biophysics, 280:80-86.
Jin et al., "Synthesis and characterizationj of hyaluronic acid-poly(ethylene glycol) hydrogels via Michael addition: an injectable biomaterial for cartilage repair," 2010, Acta Biomaterialia, 6:1968-1977.
Kalluri et al., "Characterization of microchannels created by metal microneedles: formation and closure," 2011, AAPS J, 13:4473-4481.
Kanematsu et al., "Collagenous matrices as release carriers of exogenous growth factors," 2004, Biomaterials, 24:4513-4520.
Karlin et al., "Applications and statistics for multiple high-scoring segments in molecular sequences," 1993, Proc Natl Acad Sci USA, 90:5873-5877.
Karlin et al., "Methods for assessing the statistical significance of molecular sequence features by using general scoring schemes," 1990 Proc Natl Acad Sci USA, 87:2264-2268.
Kellouche et al., "Tissue engineering for full thickness burns: a dermal substitute from bench to bedside," 2007, Biochem and Biophysical Res Comm, 363:472-478.
Kozel et al., "Elastic fibre formation: a dynamic view of extracellular matrix assembly using timer reporters," 2006, J Cell Physiol, 207:87-96.
Lanasa et al., "Influence of ECM proteins and their analogs on cells cultured on 2-D hydrogels for cardiac muscle tissue engineering," 2009, Acta Biomaterialia, 5:2929-2938.
Li et al., "Electrospinning polyaniline-contained gelatin nanofibers for tissue engineering applications," 2006, Biomaterials, 27:2705-2715.
Li et al., "Electrospun protein fibers as matrices for tissue engineering," 2005, Biomaterials, 26:5999-6008.
Liu et al., "Nanostructured Materials Designed for Cell Binding and Transduction," 2001, Biomacromolecules, 2:362-368.
Mahoney et al., "Extracellular matrix in cutaneous ageing: the effects of 0.1% copper-zinc malonate-containing cream on elastin biosynthesis," 2009, Exp Dermatol., 18(3):205-211.
Martin et al., "Total synthesis and expression in *Escherichia coli* of a gene encoded human tropoelastin," 1995, Gene, 154:159-166.
Martindale et al., Genbanc accession AAC13884, 1996.
McDevitt et al., "Spatially organized layers of cardiomyocytes on biodegradable polyurethane films for myocardial repair," 2003, Journal of Biomedical Materials Research A, 66:586-595.
Mithieux et al., "In situ polymerization of tropoelastin in the absence of chemical crosslinking," 2009, Biomaterials, 30:431-435.
Mithieux et al., "Synthetic elastin hydrogels derived from massive elastic assemblies of self-organized human protein monomers," 2004, Biomaterials, 25:4921-4927.
Mitts et al., "Aldosterone and mineralocorticoid receptor antagonists modulate elastin and collagen deposition in human skin," 2010, J Invest Dermatol, 130(10):2396-2406.
Miyagawa et al., "Tissue-Engineered Cardiac Constructs for Cardiac Repair," 2011 Annals Thoracic Surgery, 91:320-329.
Miyamoto et al., "Creation of cross-linked electrospun isotypic elastin fibers controlled cell-differentiation with new cross-linker," 2009, Int J Biol Macromolecules, 45:33-41.
Moon et al., "Preparation of Biodegradable Thermoresponsive Polyaspartamides with Nisopropylamine Pendent Groups(I)," 2006, Bull Korean Chem Soc, 27(12):1981-1984.
Nagapudi et al., "Photomediated Solid-State Cross-Linking of an Elastin-Mimetic Recombinant Protein Polymer," 2002, Macromolecules, 35:1730-1737.
Narins et al., "Persistence and Improvement of Nasolabial Fold Connection with Nonanimal-Stabilized Hyaluronic Acid 100,000 Gel Particles/mL Filler on Two Retreatment Schedules: Results up to 18 Months on Two Retreatment Schedules," 2008, Dermatological Surgery, 34:S2-S8.
Nichol et al., "Cell-laden microengineered gelatin methacrylate hydrogels," 2010, Biomaterials, 31:5536-5544.
Okamoto et al., "Characteristics of Elastin Peptides in Coacervate States: Ph Effect and Possible Ion Transport Mechanism," 1989, Peptide Chemistry, 27th ed, pp. 369-374.

(56) References Cited

OTHER PUBLICATIONS

Orner et al., "Arrays for the Combinatorial Exploration of Cell Adhesion," 2004, Journal of the American Chemical Society, 126:10808-10809.

Ostegaard et al., "Peptomers: a versatile approach for the preparation of diverse combinatorial peptidomimetic bead libraries," 1997, Mol Divers., 3:17-27.

Ostresh et al., "Generation and Use of Nonsupport-Bound Peptide and Peptidomimetic Combinatorial Libraries," 1996, Methods in Enzymology, 267:220-234.

Ozturk et al., "Dynamic cell culturing and its application to micropatterned elastin-like protein-modified poly(N-isopropylacrylamide) scaffolds," 2009, Biomaterials, 30:5417-5426.

Peppas et al., "Hydrogels in Biology and Medicine: From Molecular Principles to Bionanotechnology," 2006, Advanced Materials, 18:1345-1360.

Petite et al., "Use of diphenylphosphorylazide for cross-linking collagen-based biomaterials," 1994, Journal of Biomedical Research, vol. 28, pp. 159-165.

Raphel et al., "Photoreactive elastin-like proteins for use as versatile bioactive materials and surface coatings," 2012, Journal of Materials Chemistry, 22:19429-19437.

Rnjak et al., "Severe Burn Injuries and the Role of Elastin in the Design of Dermal Substitutes," 2011, Tissue Engineering, 17(2):81-91.

Rnjak-Kovacina et al., "Electrospun synthetic human elastin: collagen composite scaffolds for dermal tissue engineering," 2012, Acta Biomaterial, 8:3714-3722.

Sato et al., "Distinct steps of cross-linking, self-associating, and maturation of tropoelastin are necessary for elastic fiber formation," 2007, J Mol Biol, 369(3):841-851.

Shifren et al., "The Stumbling Block in Lung Repair of Emphysema: Elastic Fiber Assembly," 2006, Proc Am Thorac Soc, 3:428-433.

Shimatake et al., "Purified A regulatory protein cell positively activates promoters for lysogenic development," 1981, Nature, 292:128-132.

Smith et al., "Duration of wrinkle correction following repeat treatment with Juvederm hyaluronic acid fillers," 2010, Arch Dermatol Res, 302:757-762.

Sohm et al., "Evaluation of the efficacy of a dill extract in vitro and in vivo," 2011, Int J Cosmet Sci, 33(2):157-163.

Sreerama et al., "Estimation of Protein Secondary Structure from Circular Dichroism Spectra: Comparison of CONTIN, SELCON, and CDSSTR methods with an Expanded Reference Set," 2000, Analytical Biochemistry, 287:252-260.

Studier et al., "Use of Bacteriophage T7 RNA Polymerase to Direct Selective High-level Expression of Cloned Genes," 1986, J Mol Biol, 189:113-130.

Sykes et al., "Salt Soluble Elastin from Lathyritic Chicks," 1974, Biochem J, 141:567-572.

Tandon et al., "Electrical stimulation systems for cardiac tissue engineering," 2009, Nature Protocols, 4(2):155-173.

Thompson et al., "CLUSTAL W: improving the sensitivity of progressive multiple sequence alignment through sequence weighting, position-specific gap penalties and weight matrix choice," 1994, Nucleic Acid Research, 22(22):4673-4680.

Tourniare et al., "Polymer microarrays for cellular adhesion," 2006, Chem Comm, 2118-2120.

Vrhovski et al., "Coacervation characteristics of recombinant human tropoelastin," 1997, Eur J Biochem, 250:92-98.

Wagenseil, "New insights into elastic fiber assembly," 2007 Birth Defects Res C Embryo Today, 81(4):229-240.

Ward et al., "Thermoresponsive Polymers for Biomedical Applications," 2011, Polymers, 3:1215-1242.

Wise et al., "Engineered Tropoelastin and Elastin Based Biomaterials," 2009, Advances in Protein Chem and Structural Biol, 78:1-24.

Wu et al., "Protein Chemistry and Structure: Glycosaminoglycans Mediate the Coacervation of Human Tropoelastin through Dominant Charge Interactions Involving Lysine Side Chains," 1999, J. of Biol Chem, 274:21719-21724.

Yanagisawa et al., "Unraveling the mechanism of elastic fiber assembly: the roles of short fibulins," 2010, Int J Biochem Cell Biol, 42(7):1084-1093.

Bobroff et al., "Ten Year Experience with Use of Ilizarov Bone Transport for Tibial Defects," Bulletin—Hospital for Joint Diseases, 2003-2004, vol. 61, Nos. 3&4, pp. 101-107.

Giannoudis et al., "Bone substitutes: an update," Injury, Int. J. Care Injured, 2005, vol. 36S, pp. S20-S27.

Halm et al., "Visualizing tropoelastin in a long-term human elastic fibre cell culture model," Scientific Reports, 2016, vol. 6, 11 pages.

Lavini et al., "Bone transport and compression—distraction in the treatment of bone loss of the lower limbs," Injury, Int. J. Care Injured, 2010, vol. 41, pp. 1191-1195.

Panagiotis, "Classification of non-union," Injury, Int. J. Care Injured, 2005, vol. 36S, pp. S30-S37.

Pape et al., "Autologous Bone Graft: Properties and Techniques," J. Orthop. Trauma, 2010, vol. 24, pp. S36-S40.

Pearson, "Searching Protein Sequence Libraries: Comparison of the Sensitivity an Selectivity of the Smith-Waterman and FASTA Algorithms," Genomics, 1991, vol. 11, pp. 635-650.

Rnjak et al., "Primary human dermal fibroblast interactions with open weave three-dimensional scaffolds prepared from synthetic human elastin," Biomaterials, 2009, vol. 30, pp. 6469-6477.

Rossetti et al., "A novel anti-ageing mechanism for retinol: induction of dermal elastin synthesis and elastin fibre formation," International Journal of Cosmetic Science, 2011, vol. 33, pp. 62-69.

Schindler et al., "Bone remodeling during fracture repair: the cellular picture," Seminars in Cell & Developmental Biology, 2008, vol. 19, pp. 459-466.

Smith & Waterman, "Identification of Common Molecular Subsequences," J. Mol. Biol., 1981, vol. 147, pp. 195-197.

Wang et al., "Tropoelastin Incorporation into a Dermal Regeneration Template Promotes Wound Angiogenesis," Advanced Healthcare Materials, 2015, vol. 4, pp. 577-584.

Yamauchi et al., "Fibuln-4 and -5, but not Fibulin-2, are Associated with Tropoelastin Deposition in Elastin-Producing Cell Culture," Acta Histochem. Cytochem, 2010, vol. 43, No. 6, pp. 131-138.

Zeckey et al., "The Aseptic Femoral and Tibial Shaft Non-Union in Healthy Patients—an Analysis of the Health-Related Quality of Life and the Socioeconomic Outcome," The Open Orthopaedics Journal, 2011, vol. 5, pp. 193-197.

Kondo et al., "Changes in the migratory ability of human lung and skin fibroblasts during in vitro aging and in vivo cellular senescence," Mechanisms of Ageing and Development, 1992, vol. 63, pp. 223-233.

Jin et al., "Interaction of a biosurfactant, Surfactin with a cationic Gemini surfactant in aqueous solution," J Colloid Interface Sci., vol. 481, pp. 201-209.

\* cited by examiner

REGENERATION OF DAMAGED TISSUE

FIELD OF THE INVENTION

The invention relates to wound healing, in particular to improvements to re-epithelialization of wounds.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Skin is composed of two layers, the epidermis and the dermis, the latter being connected to the fatty underlying structure, the subcutaneous hypodermis. The epidermis is the thinnest and outermost component of the skin, consisting predominantly of keratinocyte cells. The dermis is a dense connective tissue composed of collagen, elastic fibers, and interfibrillar gel of glycosaminoglycans, salts, and water.

The epidermis and the dermis are interlocked by downward projecting epidermal rete ridges and upward projecting dermal papillae. They are separated by the basement membrane, a highly specialised form of extracellular matrix (ECM) composed of glycoproteins and proteoglycans.

The dermis consists of two structurally different layers: the superficial, thin papillary dermis and deeper reticular dermis. The papillary dermis consists of connective tissue containing fine elastic fibers and is shaped into small, finger-like projections known as dermal papillae that, as discussed previously, connect the dermis to the epidermis. The reticular dermis comprises dense, irregular connective tissue containing bundles of collagen interlaced into a net-like structure and thick, horizontally aligned elastic fibers.

Wound healing is a complex process in which a tissue either repairs or regenerates itself after injury. Some tissues are capable of regeneration, but may tend towards a repair mechanism involving fibrosis if the appropriate conditions are not found. Skin is one example. Other tissues are not capable of regeneration, and may only undergo repair mechanisms leading to fibrosis and scar formation.

The classic model of wound healing may be divided into three or four sequential, yet overlapping, phases: (1) hemostasis, (2) inflammatory, (3) proliferative and (4) remodeling. The proliferative phase is characterized by angiogenesis, collagen deposition, granulation tissue formation and re-epithelialization.

Angiogenesis occurs at the same time as fibroblast proliferation. Angiogenesis is imperative for other stages in wound healing because the activity of fibroblasts and epithelial cells requires oxygen and nutrients. According to the process, stem cells of endothelial cells and other vascular cells originating from the circulation and parts of uninjured blood vessels, develop pseudopodia and push through the ECM into the wound site to establish new blood vessels. Endothelial cells are attracted to the wound area by fibronectin found on the fibrin scab and chemotactically by angiogenic factors released by other cells, e.g. from macrophages and platelets when in a low-oxygen environment. To migrate, endothelial cells need collagenases and plasminogen activator to degrade the clot and part of the ECM. Zinc-dependent metalloproteinases digest basement membrane and ECM to allow cell migration, proliferation and angiogenesis. When tissue is adequately perfused, migration and proliferation of endothelial cells is reduced. Eventually blood vessels that are no longer needed die by apoptosis.

Collagen production and deposition is important because it increases the strength of the wound by providing more resistance to force than a fibrin-fibronectin clot. Also, cells involved in inflammation, angiogenesis, and connective tissue construction attach to, grow and differentiate on the collagen matrix laid down by fibroblasts. Type III collagen and fibronectin are generally beginning to be produced in appreciable amounts at somewhere between approximately 10 hours and 3 days, depending mainly on wound size. Their deposition peaks at one to three weeks. They are the predominating tensile substances until the later phase of maturation, in which they are replaced by the stronger type I collagen. Even as fibroblasts are producing new collagen, collagenases and other factors degrade it. Shortly after wounding, synthesis exceeds degradation so collagen levels in the wound rise, but later production and degradation become equal so there is no net collagen gain. This homeostasis signals the onset of the later maturation phase. In the first two or three days after injury, fibroblasts mainly migrate and proliferate, while later, as described above, they are the main cells that lay down the collagen matrix in the wound site. Origins of these fibroblasts are thought to be from the adjacent uninjured cutaneous tissue. Initially, fibroblasts utilize the fibrin cross-linking fibers that are formed by the end of the inflammatory phase to migrate across the wound, subsequently adhering to fibronectin. Fibroblasts then deposit ground substance into the wound bed, and later collagen, which they can adhere to for migration, thereby producing the basis for formation of granulation tissue. Granulation tissue functions as rudimentary tissue, and begins to appear in the wound already during the inflammatory phase, two to five days post wounding, and continues growing until the wound bed is covered. Granulation tissue consists of new blood vessels, fibroblasts, inflammatory cells, endothelial cells, myofibroblasts, and the components of a new, provisional extracellular matrix (ECM). The provisional ECM is different in composition from the ECM in normal tissue and its components originate from fibroblasts. Such components include fibronectin, collagen, glycosaminoglycans, elastin, glycoproteins and proteoglycans. Its main components are fibronectin and hyaluronan, which create a very hydrated matrix and facilitate cell migration. Later this provisional matrix is replaced with an ECM that more closely resembles that found in non-injured tissue. At the end of the granulation phase, fibroblasts undergo apoptosis, converting granulation tissue from an environment rich in cells to one that consists mainly of collagen.

The formation of granulation tissue into an open wound allows the re-epithelialization phase to take place, as epithelial cells migrate across the new tissue to form a barrier between the wound and the environment. Basal keratinocytes from the wound edges and dermal appendages such as hair follicles, sweat glands and sebacious (oil) glands are the main cells responsible for the epithelialization phase of wound healing. They advance in a sheet across the wound site and proliferate at its edges, ceasing movement when they meet in the middle.

Keratinocytes migrate without first proliferating. Migration can begin as early as a few hours after wounding. However, epithelial cells require viable tissue to migrate across, so if the wound is deep it must first be filled with granulation tissue. Thus the time of onset of migration is variable and may occur about one day after wounding. Cells on the wound margins proliferate on the second and third day post-wounding in order to provide more cells for migration.

If the basement membrane is not breached, epithelial cells are replaced within three days by division and upward migration of cells in the stratum basale in the same fashion that occurs in uninjured skin. However, if the basement membrane is ruined at the wound site, re-epithelialization must occur from the wound margins and from skin appendages such as hair follicles and sweat and oil glands that enter the dermis that are lined with viable keratinocytes. If the wound is very deep, skin appendages may also be ruined and migration can only occur from wound edges.

Migration of keratinocytes over the wound site is stimulated by lack of contact inhibition and by chemicals such as nitric oxide. Before they begin to migrate, cells must dissolve their desmosomes and hemidesmosomes, which normally anchor the cells by intermediate filaments in their cytoskeleton to other cells and to the ECM. Transmembrane receptor proteins called integrins, which are made of glycoproteins and normally anchor the cell to the basement membrane by its cytoskeleton, are released from the cell's intermediate filaments and relocate to actin filaments to serve as attachments to the ECM for pseudopodia during migration. Thus keratinocytes detach from the basement membrane and are able to enter the wound bed.

Before they begin migrating, keratinocytes change shape, becoming longer and flatter and extending cellular processes like lamellipodia and wide processes that look like ruffles. Actin filaments and pseudopodia form. During migration, integrins on the pseudopod attach to the ECM, and the actin filaments in the projection pull the cell along. The interaction with molecules in the ECM through integrins further promotes the formation of actin filaments, lamellipodia, and filopodia.

Epithelial cells climb over one another in order to migrate. This growing sheet of epithelial cells is often called the epithelial tongue. The first cells to attach to the basement membrane form the stratum basale. These basal cells continue to migrate across the wound bed, and epithelial cells above them slide along as well. The more quickly this migration occurs, the less of a scar there will be.

Fibrin, collagen, and fibronectin in the ECM may further signal cells to divide and migrate. Like fibroblasts, migrating keratinocytes use the fibronectin cross-linked with fibrin that was deposited in inflammation as an attachment site to crawl across.

As keratinocytes migrate, they move over granulation tissue but underneath the scab (if one was formed), separating it from the underlying tissue. Epithelial cells have the ability to phagocytose debris such as dead tissue and bacterial matter that would otherwise obstruct their path. Because they must dissolve any scab that forms, keratinocyte migration is best enhanced by a moist environment, since a dry one leads to formation of a bigger, tougher scab. To make their way along the tissue, keratinocytes must dissolve the clot, debris, and parts of the ECM in order to get through. They secrete plasminogen activator, which activates plasminogen, turning it into plasmin to dissolve the scab. Cells can only migrate over living tissue, so they must excrete collagenases and proteases like matrix metalloproteinases (MMPs) to dissolve damaged parts of the ECM in their way, particularly at the front of the migrating sheet. Keratinocytes also remodel the basement membrane by proteolytic degradation, using instead the new ECM laid down by fibroblasts to crawl across.

As keratinocytes continue migrating, new epithelial cells must be formed at the wound edges to replace them and to provide more cells for the advancing sheet. Proliferation behind migrating keratinocytes normally begins a few days after wounding and occurs at a rate that is 17 times higher in this stage of epithelialization than in normal tissues. Until the entire wound area is resurfaced, the only epithelial cells to proliferate are at the wound edges.

Growth factors, stimulated by integrins and MMPs, cause cells to proliferate at the wound edges. Keratinocytes themselves also produce and secrete factors, including growth factors and basement membrane proteins, which aid both in epithelialization and in other phases of healing. Growth factors are also important for the innate immune defense of skin wounds by stimulation of the production of antimicrobial peptides and neutrophil chemotactic cytokines in keratinocytes.

Keratinocytes continue migrating across the wound bed until cells from either side meet in the middle, at which point contact inhibition causes them to stop migrating. When they have finished migrating, the keratinocytes secrete the proteins that form the new basement membrane. Cells reverse the morphological changes they underwent in order to begin migrating; they reestablish desmosomes and hemidesmosomes and become anchored once again to the basement membrane. Basal cells begin to divide and differentiate in the same manner as they do in normal skin to reestablish the strata found in re-epithelialized skin.

Wound healing, and in particular, tissue regeneration is influenced by a range of factors and conditions. When these factors or conditions are not available, the outcome may be tissue repair and fibrosis instead of regeneration, chronic inflammation and/or ulceration. Examples of relevant factors include local factors, such as the type, size and location of the wound, and systemic factors such as adequacy of vascular supply, presence of infection, movement and metabolic status.

Hashimoto et al. 2004, *Biomaterials* 25:1407-1414 discusses the use of hybrid peptides in re-epithelialization of a wound. Notably, the study showed that an elastin derived peptide, VGVAPG showed no increase in re-epithelialization or volume of regenerated tissue compared to a negative control. The study demonstrates a preference of laminin derived peptides for wound healing, in the context of both re-epithelialization of wounds and granulation tissue formation effective for supporting re-epithelialization.

There remains a need for improvements in, or alternative approaches to wound healing, particularly skin wounds or wounds of dermal tissue.

In particular, there is a need for improvements in re-epithelialization of wounds.

There is also a need to accelerate the wound healing process, for example by improving or accelerating the rate of progression of the processes that underpin wound healing, and in particular, re-epithelialization and the like.

SUMMARY OF THE INVENTION

The invention seeks to address one or more of the above mentioned needs, or to provide an improvement in wound healing and in one embodiment provides a method of healing a wound including:
  providing an individual having a wound, the wound including a plurality of epidermal cells located about the wound thereby forming a wound edge;
  contacting the wound edge with a therapeutically effective amount of tropoelastin in conditions for enabling a sustained contact of the tropoelastin with the wound edge for a time period for enabling re-epithelialization of the wound;

wherein the re-epithelialization of the wound enables healing of the wound;

thereby healing the wound.

In another embodiment there is provided a process for improving re-epithelialization of a wound including:

providing an individual having a wound, the wound including a plurality of epidermal cells located about the wound thereby forming a wound edge;

contacting the wound edge with a therapeutically effective amount of tropoelastin in conditions for enabling a sustained contact of the tropoelastin with the wound edge for a time period for enabling re-epithelialization of the wound;

thereby improving re-epithelialization of the wound.

In another embodiment there is provided a method of minimising scar tissue including:

providing an individual having scar tissue:

forming a wound in the scar tissue, the wound including a plurality of epidermal cells located about the wound thereby forming a wound edge;

contacting the wound edge with a therapeutically effective amount of tropoelastin in conditions for enabling a sustained contact of the tropoelastin with the wound edge for a time period for enabling re-epithelialization of the wound;

wherein the re-epithelialization of the wound minimises the scar tissue;

thereby minimising scar tissue.

In another embodiment there is provided tropoelastin for use in healing a wound, or for use in improving re-epithelialization of a wound, wherein a therapeutically effective amount of tropoelastin is contacted with a wound edge in conditions for enabling a sustained contact of the tropoelastin with the wound edge for a time period for enabling re-epithelialization of the wound.

In another embodiment there is provided a use of tropoelastin for healing wound, or for improving re-epithelialization of a wound, wherein a therapeutically effective amount of tropoelastin is contacted with a wound edge in conditions for enabling a sustained contact of the tropoelastin with the wound edge for a time period for enabling re-epithelialization of the wound.

In another embodiment there is provided a use of tropoelastin in the manufacture of a medicament for healing a wound, or for improving re-epithelialization of a wound, wherein a therapeutically effective amount of tropoelastin is contacted with a wound edge in conditions for enabling a sustained contact of the tropoelastin with the wound edge for a time period for enabling re-epithelialization of the wound.

In the above described embodiments, the tropoelastin may be provided for contact with the wound edge, but not the wound bed.

In the above described embodiments, the tropoelastin may be provided in monomeric form, or it may be provided in cross linked or non cross linked form.

In the above described embodiments, tropoelastin may be blended with a cross-linked hyaluronic acid gel to form a formulation enabling a sustained release of tropoelastin.

DETAILED DESCRIPTION OF THE EMBODIMENTS

Figure 1:
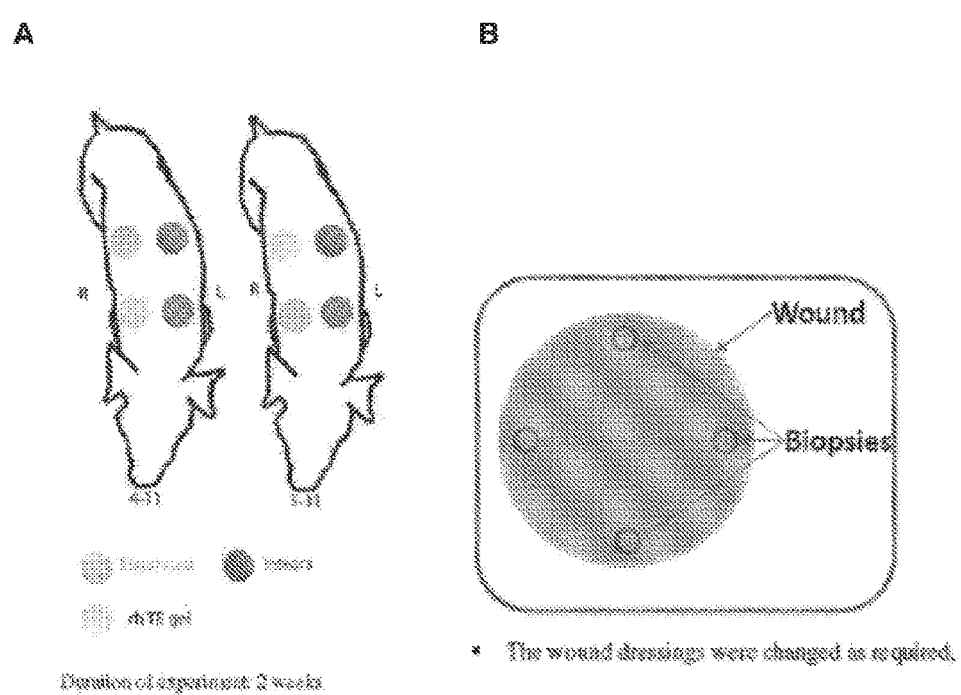
FIG. 1 (A) schematic of treatment of wounds on pigs. Wounds were either covered with Integra (blue circles) or treated with Integra Dermal Template incorporating 10% rH TE (Elastinised Integra; green circles) or Integra Dermal Template laid over a 4% rH TE Hydrogel (yellow circles). (B) Schematic of wound biopsy and dressing sites.

The inventors have found that tropoelastin improves re-epithelialization in full thickness skin wounds.

Importantly, as shown in the examples herein, the inventors have found that contact of the tropoelastin with the wound edge in the form of the epidermal cells that form a margin about the wound is critical for improvement in skin re-epithelialization. Critically, where tropoelastin is provided to the wound bed with limited sustained contact with the wound edge, there is little if any improvement in re-epithelialization of the wound.

While not wanting to be bound by hypothesis, the inventors consider that it is the sustained or persistent contact of tropoelastin with the wound edge or at least persistent placement in the vicinity of the wound edge which provides for the improvements in wound healing seen herein. Again, while not wanting to be bound by hypothesis, it is believed that when placed in contact with the wound edge or located in the vicinity thereof, the various proteases expressed during the wound healing process may generate proteolytic fragments of tropoelastin or facilitate the release of monomers of tropoelastin that favour the various processes of wound healing and tissue regeneration. The examples herein show that these processes include neovascularisation, cell chemotaxis, migration and proliferation and formation of ground substance.

The improvements in re-epithelialization are important because from both therapeutic and cosmetic perspectives, it may be critical that a wound is closed with functional epidermal tissue. Where wound closure is not seen, there is a danger that the tissue regeneration process tends to become more akin to tissue repair and fibrosis, leading to the formation of tissue having substandard function and appearance. There is also a danger of chronic inflammation and ulceration. The improvements in epithelialization in terms of extent of re-epithelialization and time to re-epithelialization are significant in this context.

It is believed that the findings described above are particularly surprising because to date, although there has been limited earlier in vitro data on the bioactivity of elastin-derived peptides, earlier in vivo wound models have demonstrated that elastin-derived peptides such as VGVAPG are ineffective for obtaining the improvements described herein. See for example Hashimoto supra. While not wanting to be bound by hypothesis, and at least to the extent relevant to wound re-epithelialization, it is believed that the failure to locate these peptides according to the wound architecture described herein has meant that the improvements described herein did not arise in these earlier studies.

Thus in one embodiment there is provided a method of healing a wound. The method includes providing an individual having a wound. The wound may arise from any injury to skin tissue. Examples of injury include burn, laceration, abrasion, incision, puncture or rupture.

Generally the injury is one which causes breakage, rupture or wounding of the epidermal and dermal layer. It may also cause wounding of tissue underlying the dermis, including subcutaneous tissue, muscle or bone. Thus the wound may be a superficial wound, a partial thickness wound or a full thickness wound.

Generally the invention applies to the regenerative processes applying to the dermal and epidermal regions including granulation tissue formation and associated processes including angiogenesis, collagen deposition and the like, and re-epithelialization.

The injury may be deliberate, for example surgical, or accidental, for example, trauma.

The wound includes a plurality of epidermal cells located about the wound thereby forming a wound edge. Typically the injury will form a wounded region of tissue characterised by an absence of epithelial cells that would normally form an epidermal layer over the region in which the wound is formed. The tissue that is substantially uninjured, and located about the site of the injury generally contains a normal epidermal layer of epidermal cells. It is these cells that are adjacent the wound that form the wound edge. As generally understood, the wound edge or wound margin becomes a site of epithelial cell proliferation during the re-epithelialization process.

According to the invention, the wound edge or wound margin is contacted with tropoelastin or elastin-derived fragments in conditions for enabling a sustained contact of the tropoelastin with the wound edge. This is believed to be an important step in the invention. As described in the examples herein, re-epithelialization tends to be observed where the tropoelastin is in contact with, or located in the vicinity of the wound edge. For example, the re-epithelialization may be more complete or naturally structured and the rate of re-epithelialization may be accelerated. Some of these characteristics are not seen, for example, when the tropoelastin is placed in contact with the wound bed only.

As described herein, the wound bed is generally a dermal tissue surface arising from injury on which granulation tissue is eventually formed in a functional regenerative process. By 'located in the vicinity of the wound edge' it is meant that the tropoelastin is provided so that it or various proteolytic fragments thereof are located so close to the wound edge as to readily permit diffusion of tropoelastin or proteolytic fragments thereof for contact with the wound edge. In this context, the location of the tropoelastin or elastin-derived fragments thereof, only in or on the wound bed, is shown herein not to provide for re-epithelialization as may be observed when the tropoelastin is added to the wound edge. Therefore administration of tropoelastin to the wound bed only is not seen according to the invention as being a location of tropoelastin in the vicinity of the wound edge.

There are a number of approaches to enabling contact of the tropoelastin or elastin-derived fragments with the wound edge. In one embodiment, the tropoelastin is provided in the form that enables persistent contact with the wound edge. For example, the tropoelastin may be provided in the term of a gel having a viscosity or an adherence which enable the gel, and accordingly, the tropoelastin or fragment therein, to remain in contact with the wound edge. Examples of particular gel formulations include those generally discussed in WO2012068619.

In another embodiment the tropoelastin is provided in or on a solid phase, such as a dressing, stent, device or the like which is adapted for sustained contact of the solid phase (and therefore the tropoelastin located in or on the solid phase) with the wound edge. For example a solid phase such as a scaffold, bulking agent or prosthesis may be placed in the wound bed so that the apical surface of the scaffold is aligned with the wound edge, enabling the tropoelastin or elastin derived peptide in gel format or other to be provided on the apical surface of the scaffold or like in contact with the wound edge. Examples of particular solid phase arrangements include those involving electrospinning of tropoelastin, optionally with other connective tissue molecules such as collagen, and those involving co-precipitation with another connective tissue molecule such as a collagen.

In an alternative approach, it is the conditions themselves in which the tropoelastin is provided that enable the sustained contact of the tropoelastin with the wound edge. For example, the tropoelastin may be provided in a solvent which is sprayed or painted onto the wound edge, and then conditions are provided for evaporation of the solvent from the wound edge, leaving the tropoelastin or fragment thereof in contact with the wound edge.

The tropoelastin or elastin derived fragment is typically provided in a therapeutically effective amount. This is generally any amount that results in an improvement in re-epithelialization, in the context of either the extent of re-epithelialization, or time to complete re-epithelialization, as compared with the extent of, or time to re-epithelialization in circumstances where the tropoelastin or elastin derived fragment is not so provided. Generally tropoelastin is provided in a concentration of about 0.1 mg/ml to 250 mg/ml, although this will depend on various factors relevant to the regeneration of skin tissue discussed above. Within this range, the following concentrations may be particularly useful, 1 mg/ml, 25 mg/ml, 50 mg/ml, 100 mg/ml, 150 mg/ml and 200 mg/ml.

Thus, in one embodiment there is provided a method of healing a wound including:
    providing an individual having a wound, the wound including a plurality of epidermal cells located about the wound thereby forming a wound edge;
    contacting the wound edge with tropoelastin in a concentration of about 0.1 mg/ml to 250 mg/ml in conditions for enabling a sustained contact of the tropoelastin with the wound edge for a time period for enabling re-epithelialization of the wound; wherein the re-epithelialization of the wound enables healing of the wound; thereby healing the wound. In this embodiment, the tropoelastin may be provided for use in the farm which can be applied to the wound edge for sustained contact of the tropoelastin with the wound edge. Such a form may be a gel. Preferably in this embodiment the tropoelastin is provide in sustained contact with the wound edge for a period of no more than about 1 to weeks, preferably with no contact with the wound bed.

In accordance with the invention, the tropoelastin or elastin derived peptides are provided for a time period enabling re-epithelialization of the wound. The time period is generally dependent on the nature of the wound and other factors relevant to tissue regeneration noted above. Where the wound is a minor acute wound arising from trauma, it may be necessary to provide the tropoelastin in sustained contact with the wound edge for a period of time of no more than about 1 to 2 weeks. This may require a once only application of the tropoelastin. The same may apply where the wound is a clean surgical wound, although this would depend on the size and nature of the wound. Where the wound is more complex, for example resulting in a substantial loss of dermal tissue or underlying tissue, for example as in a major trauma or chronic injury, it may be necessary to provide the tropoelastin according to a dosage schedule, far example aligned with the time period during which the wound is routinely dressed and cleaned. In the circumstances it may be necessary to add the tropoelastin to the wound edge daily for a time period of 1 to 3 weeks or more or in a form which enables sustained release of a therapeutically effective amount of tropoelastin at the wound edge for 1 to 3 weeks or more.

In the above embodiment of the invention it is the improved re-epithelialization of the wound arising from sustained contact of tropoelastin with the wound edge during the wound healing process that results in the healing of the wound. In the embodiment, and as established by the examples herein, it is possible to improve re-epithelialization without substantial contact of the tropoelastin with the wound bed.

As generally understood, a wound bed is generally termed in the dermal layer and may extend to subcutaneous layers or other layers located beneath the dermal layer. A wound bed as generally understood is that surface of normal uninjured tissue, in particular, dermal tissue that is located within the wound. The wound bed may be otherwise defined as that part of the wound in which granulation tissue formation occurs. The wound bed does not generally include epidermal tissue, and therefore the wound bed does not itself contain a 'wound edge' as referred to herein. In more detail, as is generally understood, all skin wounds in which the dermal layer has been penetrated (such as a partial or full thickness wound) will have a wound edge and a wound bed. Skin wounds that are superficial will have a wound edge but not a substantial wound bed (indeed, a superficial wound may simply have exposed, but otherwise uninjured dermal tissue). Therefore, as generally understood and in accordance with the invention, 'wound edge' and 'wound bed' are two different concepts.

One particular application of the invention described herein is in the remodeling or substantial removal of scar and related fibrotic tissue. As is generally understood, scar tissue arises as a consequence of tissue repair. The end result is the formation of a tissue structure that lacks the structure and functional aspects of the relevant tissue in which the scar or fibrosis is located. In particular, the finding that with location of tropoelastin or an elastin derived fragment relative to wound architecture described herein it then becomes possible to induce key aspects of tissue regeneration, it then becomes possible to induce a wound and then a wound healing process in scar tissue. Therefore, in another embodiment there is provided a method of minimising scar tissue including:
    providing an individual having scar tissue;
    forming a wound in the scar tissue, the wound including a plurality of epidermal cells located about the wound thereby forming a wound edge;
    contacting the wound edge with a therapeutically effective amount of tropoelastin in conditions for enabling a sustained contact of the tropoelastin with the wound edge for a time period for enabling re-epithelialization of the wound;
    wherein the re-epithelialization of the wound minimises the scar tissue;
    thereby minimising scar tissue.

In one embodiment the minimisation of scar tissue refers to removal of scar tissue. In another embodiment the scar tissue is minimised by minimising the volume of, or minimising the abundance of scar tissue in a given region of skin.

The wound may be created by various techniques known in the art. One particularly preferred technique involves forming a plurality of micro punctures along the scar tissue so as to create multiple wounds in the scar. The tropoelastin or elastin derived peptide is then provided in sustained contact with the wound edge, or wound bed to enable tissue regenerative processes described herein.

In one embodiment, the tropoelastin is provided in a form whereby the tropoelastin monomers are not cross linked.

In another embodiment the tropoelastin is provided in the form of a composition that does not include lysyl oxidase or other cross linking reagent.

In another embodiment the tropoelastin is provided in form of a composition that does not include amino acid based antioxidants.

Generally the tropoelastin for use in the invention is recombinant or synthetic tropoelastin and it is provided in a cell free composition.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1 Dermal Regeneration Full Thickness Surgical Wounds

The current study assessed the impact of recombinant human tropoelastin (rH TE) on dermal regeneration of full thickness surgical wounds in a pig model following the application of Integra Dermal Template with and without rH TE. Analysis of the regenerated dermis at two weeks revealed that the presence of rH TE in Integra Dermal Template led to an improved wound repair process. The improvement was marked by increased numbers of fibroblast, elevated collagen deposition, increased vascularization of the regenerated dermal tissue, and an increased level of detected elastin fibers in the regenerated dermis. These events were accompanied by increased keratinocyte proliferation resulting in improved epithelialisation of the wound due to the presence of rH TE.

Materials and Methods

Test Items

Three products were assessed in the current study:
Control: Integra Dermal Template
Test A: Integra Dermal Template incorporating 10% rH TE Elastinised Integra)
Test B: Integra Dermal Template laid over a 4% rH TE Hydrogel Full Thickness Porcine Model
Two pigs were utilized in the current study, each with four wound sites, two on each side of the animal as illustrated in the image below.
For each pig, two wounds from one side were covered with Integra and two wounds from the other side were treated as test A and B as indicated in FIG. 1A.
Day 0
    Four full thickness excisional circular wounds with 5 cm in diameter were created on the upper backs of each pig as noted in the diagram above.
    Each wound was treated with either the control Integra Dermal template or Test Item A or B as noted in the diagram above.
Day 7 (week 1)
    Dressing changes for all wounds.
Day 14 (week 2)
    4 mm biopsies were taken from each wound site a few mm away from the edge of the wounds as depicted in FIG. 1B.

Wound Analysis

Sampling at the wound site was first undertaken two weeks after surgery and treatment. Biopsy of the wound site was conducted as described above. Samples were subjected to histopathology and immunohistochemistry analysis to assess fibroblast infiltration, collagen and elastin deposition, vascularization of the regenerated tissue and regeneration of the epithelium.

Results

Fibroblast Infiltration of the Integra Dermal Template

Fibroblast numbers had increased in all constructs but were more elevated in the presence of rH TE. The effect was most marked in the Elastinised Integra, where rH TE permeated the entire construct.

Collagen and Elastin Deposition

Figure 2:
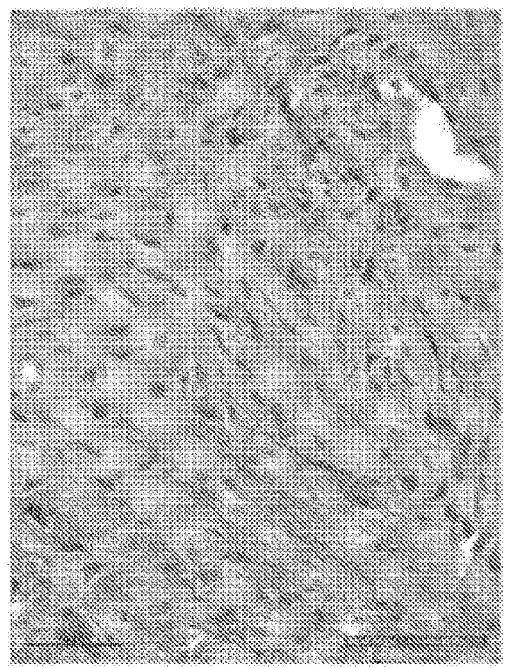
FIG. 2: biopsy section stained with VVG from a site treated with Elastinised Integra showing the presence of fibroblast cells, new collagen deposition and the presence of elastin fibers.

Enhanced fibroblast levels led to increased collagen deposition in the presence of rH TE as evidenced by hematoxylin and eosin (H&E) and Verhoeff-Van Gieson (VVG) staining as shown in FIG. 2.

The presence of elastin (i.e. not rH TE) in biopsy sections taken from each of the treated sites was assessed by VVG staining of biopsy sections. Because it was not possible to accurately distinguish endogenous elastin fibers from those that may have been regenerated during the dermal repair process, tissue sections from each treatment site were simply scored for the presence or absence of elastin fibers in the repaired dermal tissue. The total number of sections analyzed in the study for Integra Dermal Template alone, Integra Dermal Template plus 4% rH TE hydrogel and Elastinised Integra were 32, 16 and 16, respectively. The results are summarized in Table 1 below.

Table 1. Number of VVG-stained biopsies sections analyzed in which elastin fibers were detected in the dermis.

| Treatment | Sections in which elastin fibers were detected in the neo-dermis |
|---|---|
| Integra Dermal Template alone | 2/32 (5.25%) |
| Integra Dermal Template + 4% TE Gel | 8/16 (50%) |
| Elastinised Integra | 4/16 (25%) |

Figure 3:
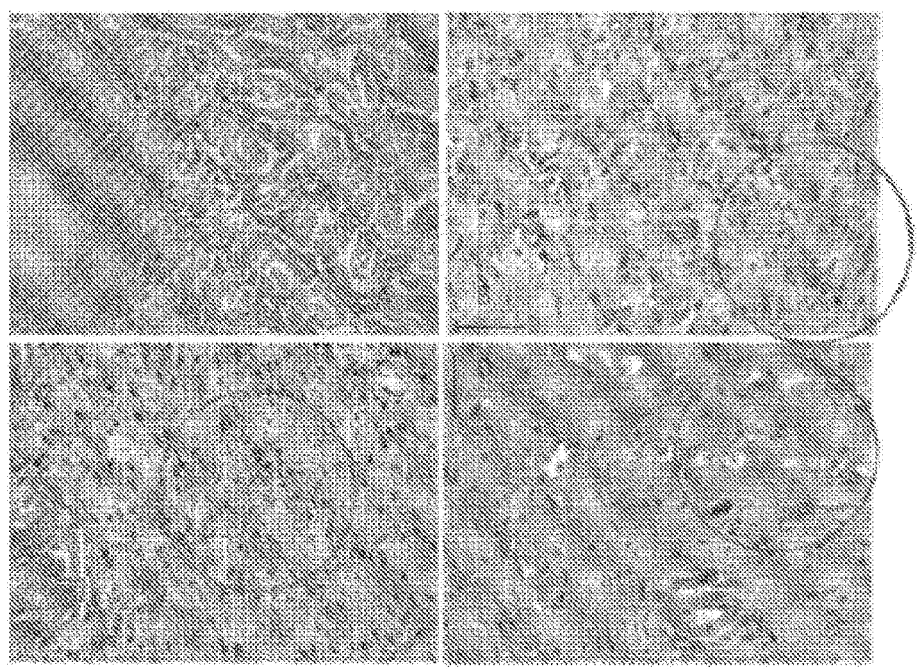
FIG. 3: comparison of different types of dermis observed in VVG stained core biopsy samples taken two weeks post-surgery. A) Original Dermis; B) Dermis that is half-way in appearance between newly formed and normal (circled); C) Dermis of newly formed appearance (circled: less eosinophilic staining, collagen fibers appear thinner and less organized, more cellular than dermis of normal appearance); D) Dermis of normal appearance (circled: more eosinophilic staining, collagen fibers appear thicker and more organized, less cellular than dermis that appears newly formed.)
Figure 4:
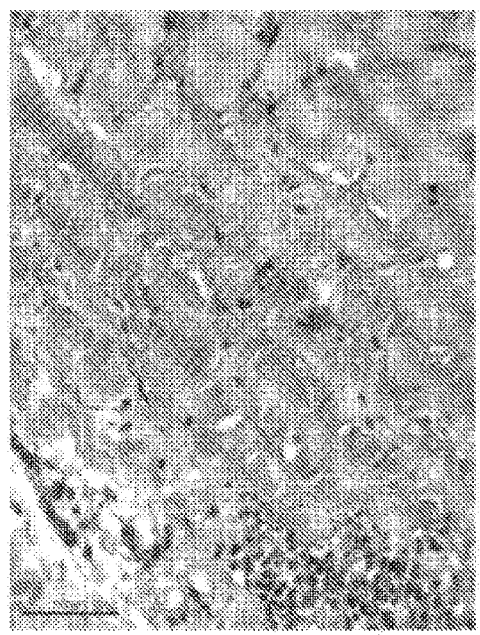
FIG. 4: tissue section from wound site treated with Integra Dermal Template+4% rH TE hydrogel two weeks post-surgery. Elastin fibers can be seen towards the base of the dermis underneath the visible rH TE gel in dermal tissue of what looks to be normal appearance. Dermal tissue of similar appearance was also seen within the TE hydrogel.

Examples of the dermal tissue encountered during the analysis of the VVG stained biopsy sections are provided in FIG. 3. In addition, an example of elastin fibers present in dermal tissue adjacent to the rH TE hydrogel is provided in FIG. 4.

Vascularization of the Regenerated Dermis

Figure 5:
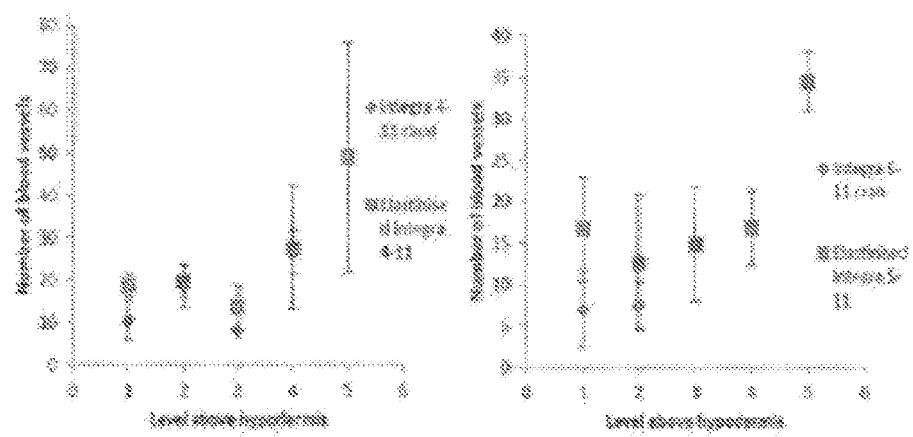
FIG. 5: a comparison of the number of blood vessels in each layer of dermis in core biopsy samples taken 2 weeks post-surgery. Elastinised Integra was compared to the corresponding cranial (cran) or caudal (caud) control Integra Dermal Template alone from the same pig. The VVG-stained core biopsy samples were examined under 100× magnification and assessed using ImageJ software. Micrographs were taken at multiple levels in the dermis. The first level of dermis (level 1) was obtained by moving the field of view seen in the camera so that the hypodermic was just out of view. Subsequent levels were obtained by moving the sample 0.5 FOVs (as observed down the microscope) towards the epidermis. Thus, level 2 above the hypodermis is 0.5 FOVs (as observed down the microscope) away from the level 1 image. Three images were taken at each level of the dermis: one at either edge of the sample and one in the middle. This method ensured that the images taken at different levels of dermis would not contain the same blood vessels, as each FOV down the microscope had a diameter of 2.5 mm, whereas each image as taken by the camera was 650 µm wide. Criteria for blood vessels were: a) lumen size had to be equal to or greater than 10 µm; and, b) the lumen had to be lined by at least 2 cells with dark elongated nuclei. The identity of vessels was sometimes positively confirmed by the presence at blood cells within the lumen, and/or the presence of smooth muscle cells in the tunica media of the vessel wall.

The level of vascularization in the regenerated dermis was assessed by histopathology. The number of blood vessels at different levels of the biopsy section tissue was assessed under the microscope, starting with the hypodermic and moving progressively towards the epidermis as described in FIG. 5. As can be seen from the data presented in FIG. 5, the presence of rH TE in the Integra Dermal Template (Elastinised Integra) resulted in an increased number of blood vessels in the regenerated tissue particularly in the direction of the superficial dermis when compared to sites treated with Integra Dermal Template. A similar trend was seen with the sites treated with Integra Dermal Template on top of a 4% rH TE gel.

Epithelial Regeneration

Figure 6:
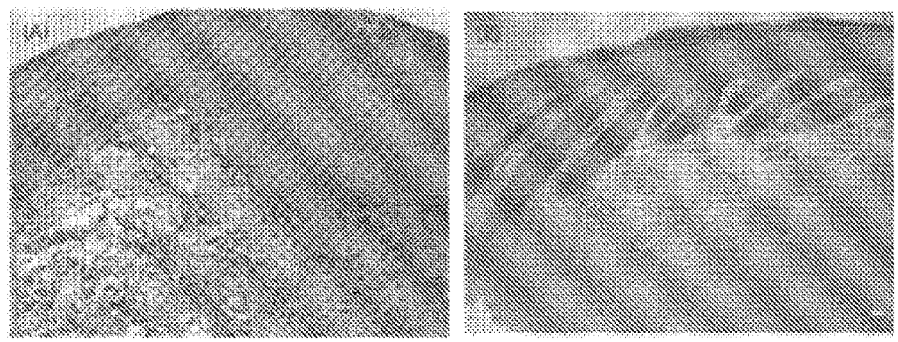
FIG. 6: (A) Example of small projections of epidermis into the dermis in a sample treated with Integra only. (B) Example of Rete-like ridges of epidermis in an Elastinised Integra sample.

The regeneration of the epithelium at the wound sites was one of the most striking benefits of the Elastinised Integra over the other test and control items. As detailed in Table 2, and depicted in FIG. 6, the Elastinised Integra resulted in an almost complete re-epithelialization of the wound site by Week 2, and was accompanied by the presence of rete—like ridges indicative of a more natural dermal-epidermal junction.

Table 2. Epithelium features of core biopsy samples collected at two weeks post-surgery were observed at 100× magnification. A total of 16 Integra samples, 8 TE gel+ Integra samples and 8 Elastinised Integra samples were examined. The presence of complete or partial epithelialization within each core biopsy sample was recorded. Epithelia with sparse ridges were classed as separate from those with well-developed and dense ridges (ridges in part of epithelium and ridges in all of epithelium, respectively).

|  | Presence of Epithelium |  | Presence of Rete - Like Ridges |  |  |  |
|---|---|---|---|---|---|---|
| Treatment | Partial | Complete | In part of epithelium | In all of epithelium | Small projections only | Prominent ridges |
| Integra alone | 18.8% | 0.0% | 12.5% | 0.0% | 6.3% | 6.3% |
| Integra + rH TE | 12.5% | 0.0% | 12.5% | 0.0% | 0.0% | 12.5% |
| Elastinised Integra | 12.5% | 75% | 12.5% | 62.5% | 12.5% | 62.5% |

Conclusions and Discussion

Figure 7:
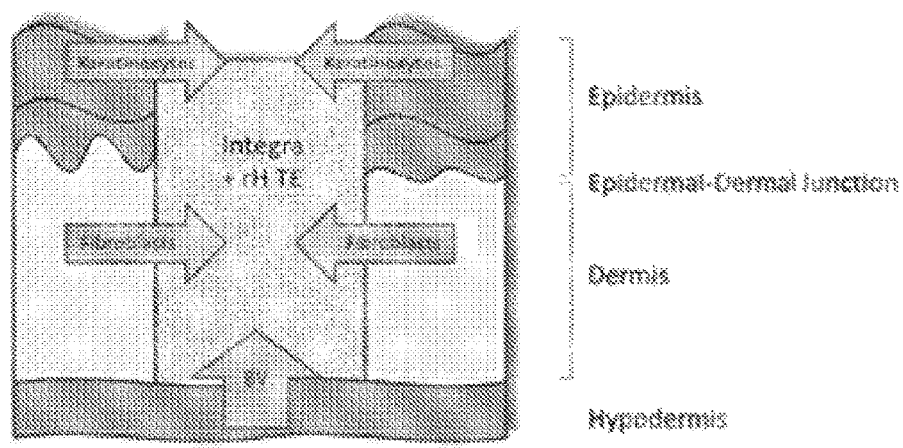
FIG. 7: Recombinant human tropoelastin is proposed to contribute to the wound repair process via chemotactic signaling which contributes to fibroblast & keratinocyte recruitment and vascularization of the regenerated tissue.

The data are explained by a model, as depicted in FIG. 7, where rH TE provides a biological stimulus to the dermal repair process when incorporated into Elastinised Integra. This leads to a greater level of fibroblast infiltration, neovascularization of the regenerated tissue and epithelialisation of the wound site. These benefits mean that the use of Elastinised Integra may preclude the need for skin grafting. This biological stimulus is consistent with the known properties of rH TE in contributing to the tissue repair process as tropoelastin is chemotactic to cells involved in the tissue repair process including monocytes (contribute to neovascularization, differentiate into e.g., fibrocytes) and fibroblasts [Almine et al., 2012].

Confirmation that the effects were due to the presence of rH TE came from the Integra Dermal Template+4% rH TE hydrogel, which showed a similar trend for increased fibroblast infiltration and neovascularization. As expected for the localized delivery with the hydrogel, the effects were limited to the deeper dermis where the rH TE-containing gel was applied. As these effects were primarily constrained to deeper layers of the dermis, epithelial regeneration was not seen; i.e. the rH TE gel was separated from the superficial dermis and epidermis by the Integra Dermal Template. We saw more elastin fibers in these biopsies of the regenerated dermis. This is likely due to a sustained release of rH TE. The rH TE gel contains full length tropoelastin monomer which is unmodified and gradually leaches from the gel, supplying tropoelastin that may be utilized by regenerative fibroblasts to construct elastic fibers. Primary human skin fibroblasts utilize rH TE as a substrate for cellular growth and remodel the rH TE into elastin fibers in a process which is dependent on lysyl oxidase (whose activity is inhibited by BAPN) and which results in mature elastin fibers (as evidenced by measurements of elasticity and characteristic fluorescence properties for elastin fibers) [Weiss lab, unpublished data].

In conclusion, and recognizing that these studies are conducted on a small number of animals, it appears that the incorporation of rH TE into the Integra Dermal Template can substantially accelerate dermal and epidermal regeneration.

Example 2: Use of Electrospun, Co-Precipitate and Gel Based Formulations

Pigs were utilized in the current study, each with four, circular, 5 cm diameter, wound sites, two on each side of the animal. For each pig, two wounds From one side were covered with a commercially available skin template product, and two wounds from the other side were treated with either test item A, B or C.

Day 0
    Four full thickness excisional circular wounds with 5 cm in diameter were created on the upper backs of each pig as noted in the diagram above.
    Each wound was treated with either the control skin template or Test Item A, B or C.
Day 7 (week 1)
    Dressing changes for all wounds.
Day 14 (week 2)
    4 mm biopsies were taken from each wound site a few mm away from the edge of the wounds as depicted in FIG. 1B.

Wound Analysis

Sampling at the wound site was first undertaken two weeks after surgery and treatment. Biopsy of the wound site was conducted as described above. Samples were subjected to histopathology and immunohistochemistry analysis to assess fibroblast infiltration, collagen and elastin deposition, vascularization of the regenerated tissue and regeneration of the epithelium.

Preparation of Test Item A: Electrospun Scaffolds

Different proportions of tropoelastin and collagen were combined in a 20% (w/v) protein solution in 1,1,1,3,3,3-hexafluoro-2-propanol (HFP). These included 100% tropoelastin, 80% tropoelastin with 20% collagen, 60% tropoelastin and 40% collagen, 50% tropoelastin and 50% collagen, and 100% collagen. Solutions were loaded into a syringe equipped with a blunt 18 gauge needle and a flow rate of 3 ml h1 was modulated using a syringe pump. The needle was connected to a 20 kV positive power supply and directed at a grounded, 30 mm diameter circular, brass collector at a collector distance of 20 cm. Electrospun scaffolds were chemically cross-linked to stabilize their structures in aqueous environments. Scaffolds were placed in an open stage desiccator and cross-linked by vapor from a separate 25% (v/v) aqueous glutaraldehyde solution then quenched by immersion into 0.2 M glycine solution overnight. Scaffolds were then washed repeatedly in PBS. See Rnjak-Kovacina, J. et al. *Acta Biomater.* 2012 October;

8(10):3714-22. This item is significantly more cross linked than Test Item B below. It tends to be more amenable to cellular infiltration.

Preparation of Test Item B: Collagen Sponges Incorporating Tropoelastin

A white coprecipitate of type I bovine collagen mixed with 10% w/w tropoelastin in 0.05 M acetic acid (pH 3.2) was converted into a highly porous white membrane by freeze-drying. Control of the average pore diameter was achieved by adjusting the initial shelf temperature snap freezing in liquid nitrogen. Subsequent exposure of the dry solid to 105° C. and a 6 kPa vacuum over 24 hr introduced covalent crosslinks between the polypeptide chains of collagen. The construct was immersed in a bath containing 0.25% aqueous glutaraldehyde in 0.05 M acetic acid, and the collagen underwent further covalent crosslinking. The constructs were rinsed in deionized water over 24 hr. See Kanematsu, A., et al. *Biomaterials*. 2004 August; 25(18): 4513-20. This tends to be more resistant to degradation than Test item A above.

Preparation of Test Item C: Collagen Sponges with Tropoelastin Gel Underneath

Full length tropoelastin was incorporated into a hyaluronic acid gel essentially as described in WO2012068619 and filled into a syringe prior to use. The gel was applied onto the surface of an exposed wound bed, then overlaid with a collagen sponge produced as described for Test Item B but omitting the tropoelastin.

Example 3: Assessment of Epithelial Regeneration in a Porcine Needling Skin Model Pigs were each treated with up to ten 2 cm×2 cm sites across the dorsum. Each site received one of three treatment methods:
1) Site A: Received puncture wounds using a micro-coring needle approximately every 2 mm apart across the area of skin to be treated. Following the needle treatment a gel containing 1% to 5% w/v tropoelastin protein was applied topically to the treated area and held in place by a Tegaderm dressing to enable the gel to be retained and pass into the puncture sites.
2) Site B: Received puncture wounds using a hypodermic needle with each puncture including the injection of 0.05 to 0.5 ml of a 1 to 5% w/v tropoelastin gel into the upper dermis of the skin tissue. The puncture/injections were applied approximately 2 mm apart across the area of skin to be treated followed by wound dressing.
3) Site C: Received the implantation of 0.5 to 2 ml of a 1 to 5% w/v tropoelastin gel in the upper dermis using a cross-hatching injection technique followed by the application of puncture wounds across the treatment area using a micro-coring needle approximately 2 mm apart.

Photographs and punch biopsies were performed at day 0, 7, and 28. Samples were subjected to histopathology and immunohistochemistry analysis to assess fibroblast infiltration, collagen and elastin deposition, vascularization of the regenerated tissue and regeneration of the epithelium.

Example 4: Assessment of Epithelial Regeneration Following Laser Assisted Delivery of Tropoelastin to a Porcine Skin Model Fractional laser resurfacing creates vertical channels in the skin approximately 3 mm deep that assists in the delivery of topically applied drugs to the skin. Pigs were each treated with up to ten 2 cm×2 cm sites across the dorsum. Each site was treated with a fractional single hole $CO_2$ laser essentially as described by Haedersdal et al 2010 (*Lasers Surg Med*. 42(2):113-22). Subsequent to laser treatment, the test sites received either:
  A hyaluronic acid gel containing 1 to 5% w/v tropoelastin; or
  A hyaluronic acid gel control Photographs and punch biopsies were performed at day 0, 7, and 28. Samples were subjected to histopathology and immunohistochemistry analysis to assess fibroblast activity, collagen and elastin deposition, vascularization and regeneration of the epithelium.

REFERENCES

Almine et al 2012. Elastin Signaling in Wound Repair. Birth Defects Research (Part C) 96:248-257.

The invention claimed is:
1. A method of healing a wound including: providing an individual having a wound, the wound including a plurality of epidermal cells located about the wound thereby forming a wound edge; and
  contacting the wound edge with a therapeutically effective amount of a composition comprising tropoelastin, the composition comprising a crosslinked hyaluronic acid gel and tropoelastin monomers that are not crosslinked, wherein the composition provides for a sustained release of the tropoelastin, and wherein the corn position is in contact with the wound edge for a time period to promote re-epithelialization of the wound.
2. The method of claim 1, wherein the time period is no more than about 1 to 2 weeks.
3. The method of claim 1, wherein the time period is about 1 to 3 weeks.
4. The method of claim 1, wherein the composition comprises about 0.1 mg/mL to about 250 mg/mL of tropoelastin.
5. The method of claim 1, wherein the re-epithelialization of the wound enables healing of the wound.
6. The method of claim 1, wherein the wound is from an injury to skin tissue.
7. The method of claim 6, wherein the injury causes breakage, rupture or wounding of an epidermal layer or a dermal layer.
8. The method of claim 1, wherein the wound is a superficial wound, a partial thickness wound, or a full thickness wound.
9. The method of claim 1, wherein the composition is provided in or on a solid phase.
10. The method of claim 9, wherein the solid phase is a dressing, stent, scaffold, bulking agent, or prosthesis.
11. The method of claim 1, wherein the wound is from surgery.

* * * * *